United States Patent [19]
Silverman et al.

[11] Patent Number: 6,162,825
[45] Date of Patent: *Dec. 19, 2000

[54] HIGH FRUCTOSE INSECTICIDE BAIT COMPOSITIONS

[75] Inventors: Jules Silverman, Walnut Creek, Calif.; Donald N. Bieman, Cayey, Puerto Rico

[73] Assignee: The Clorox Company, Oakland, Calif.

[*] Notice: This patent is subject to a terminal disclaimer.

[21] Appl. No.: 09/292,996

[22] Filed: Apr. 16, 1999

Related U.S. Application Data

[60] Continuation-in-part of application No. 08/904,569, Aug. 4, 1997, Pat. No. 5,925,670, which is a division of application No. 08/629,263, Apr. 8, 1996, abandoned, which is a continuation of application No. 08/342,543, Nov. 21, 1994, Pat. No. 5,547,955, which is a continuation-in-part of application No. 07/964,994, Oct. 22, 1992, abandoned.

[51] Int. Cl.[7] .......................... A01N 43/02; A01N 25/00; A01N 57/00; A01N 57/10
[52] U.S. Cl. .............................. 514/450; 424/84; 514/75; 514/140; 514/144
[58] Field of Search .............................. 514/450, 75, 140, 514/144; 424/84

[56] References Cited

U.S. PATENT DOCUMENTS

| | | | |
|---|---|---|---|
| 3,076,744 | 2/1963 | Geary | 167/48 |
| 3,244,586 | 4/1966 | Rigterok | 167/33 |
| 3,325,355 | 6/1967 | Goodhue | 167/33 |
| 3,913,259 | 10/1975 | Nishimura et al. | 43/114 |
| 4,049,460 | 9/1977 | Broadbent | 106/15 |
| 4,087,525 | 5/1978 | Lovell | 424/244 |
| 4,279,895 | 7/1981 | Carle | 424/127 |
| 4,310,519 | 1/1982 | Albers-Schonberg et al. | 424/181 |
| 4,336,194 | 6/1982 | Ohsumi et al. | 548/562 |
| 4,386,071 | 5/1983 | Carle | 424/127 |
| 4,826,682 | 5/1989 | Sakharova | 424/623 |
| 4,834,977 | 5/1989 | Kohama et al. | 424/405 |
| 4,845,103 | 7/1989 | Spaulding et al. | 514/275 |
| 4,857,532 | 8/1989 | Koehler et al. | 514/262 |
| 4,889,710 | 12/1989 | Hagarty | 424/45 |
| 4,944,950 | 7/1990 | Sakharova | 424/623 |
| 4,985,413 | 1/1991 | Kohama et al. | 514/79 |
| 4,990,514 | 2/1991 | Bruey | 514/275 |
| 5,012,004 | 4/1991 | Takahashi et al. | 568/53 |
| 5,019,595 | 5/1991 | Yano et al. | 514/531 |
| 5,055,491 | 10/1991 | Yano et al. | 514/531 |
| 5,091,183 | 2/1992 | Yano et al. | 424/405 |
| 5,223,270 | 6/1993 | Jones | 424/659 |

OTHER PUBLICATIONS

Susan Budavari et al., "The Merck Index", *An Encyclopedia of Chemicals, Drugs, and Biologicals*, Twelfth Edition, pp. 151, 366.

*Primary Examiner*—Allen J. Robinson

[57] ABSTRACT

This invention relates to the discovery that in many strains of the German cockroach [*Blattella, germanica* (L.)], feeding is inhibited by high glucose levels, while conversely, feeding of this strain of cockroach is stimulated by high or ultra high levels of fructose. Therefore, preferred bait compositions of the instant invention relate to insecticide bait compositions for insect control which contain a ratio of fructose to glucose of no less than about 9:1 and as great as about 10:0, binder and an avermectin insecticide.

10 Claims, No Drawings

HIGH FRUCTOSE INSECTICIDE BAIT COMPOSITIONS

CROSS REFERENCE TO RELATED APPLICATIONS

This application is a continuation-in-part of U.S. patent application Ser. No. 08/904,569, filed Aug. 4, 1997, now U.S. Pat. No. 5,925,670 which is a divisional of U.S. patent application Ser. No. 08/629,263, filed Apr. 8, 1996, now abandoned which is a continuation of U.S. patent application Ser. No. 08/342,543, filed Nov. 21, 1994, now U.S. Pat. No. 5,547,955, which is a continuation-in-part of U.S. patent application Ser. No. 07/964,994, filed Oct. 22, 1992, now abandoned.

BRIEF DESCRIPTION AND BACKGROUND OF THE INVENTION

This invention pertains to an improved poison bait formulation for control of German cockroaches [*Blattella germanica* (L.)]. More particularly, this invention relates to improved insecticide, bait compositions containing high levels of fructose and very low levels of glucose for the control of German cockroach strains.

Heretofore there have been a large number of insecticide compositions. Most of them are based on chemicals which are either capable of instant and delayed killing action. These prior poison baits contain various materials as food attractants. These food attractants used in compositions include various sweetening agents, together with the toxicant. The prior art describes insecticide bait compositions containing a very general array of sugars and sweeteners as attractants for cockroach control, without regard to diversity of feeding preferences as displayed by field cockroach strains.

For example, U.S. Pat. No. 4,386,071 relates to an insecticide natural bait composition which includes, in a broad sense, sugar or sugar substitute. Similarly, U.S. Pat. No. 4,845,103 relates to an insecticide bait composition for the control of cockroaches in which the food attractant system comprises various ingredients, including a mixture of liquid food, for example, molasses, corn syrup, maple syrup, honey.

U.S. Pat. No. 4,889,710 relates to a stable aerosol foam insecticide bait composition which includes as an attractant to facilitate consumption by the crawling insects, sugars or a sugar composition.

U.S. Pat. No. 4,985,413 relates to poison bait for control of insects, particularly cockroaches, wherein the bait contains a saccharide as a component in amounts of 0.1–10% by weight and 10–40% by weight based on the total weight of the composition. Examples of saccharide in the '413 patent are sucrose, glucose, d-fructose, lactose, black sugar, brown sugar, soft brown sugar, etc. Among the preferred sugars mentioned in the '413 patent are black sugar, brown sugar and soft brown sugar. The content of the saccharide is normally preferred between 10–40% by weight.

Without regard for the toxicant in the instant bait composition, it has been found that bait compositions having ultra high fructose to glucose ratios are more efficacious than those with lower fructose to glucose ratios. More particularly, it has been found that improved consumption performance of cockroach baits by field-collected cockroaches, has been found with bait compositions containing fructose to glucose ratios in excess of about 9:1, respectively. When fructose to glucose ratios are less than 9:1, feeding inhibition has been observed. Therefore by "ultra high" is meant a ratio of fructose to glucose in no less than 9:1 to about 10:0. Preferably, about 40% by weight of the total formulation is fructose.

A preferred embodiment of this invention are bait compositions having ultra high fructose content within the definition herein defined and a nonrepellent binder and from about 0.005% to about 1.0% of a cockroach effective toxic insecticide compound. Preferably the cockroach insecticide compound is an avermectin.

More preferably, the present invention provides such an insecticide—bait composition containing ultra high ratio levels fructose to glucose in the range of from 9:1 to 10:0, respectively, about 40% by weight of the total formulation is fructose and about 0.005% to about 1.0% of an avermectin insecticide. Most preferably, this insecticide—bait composition contains from about 0.01 % to about 0.5% of an avermectin insecticide.

Therefore, as the result of extensive studies with regard to cockroach bait containing very general arrays of sugars and sweeteners as attractants or feeding stimulants, it has been discovered that in many strains of the German cockroach [*Blattella germanica* (L.)], feeding is inhibited by moderate to high glucose levels. Conversely, feeding of these cockroach strains is stimulated by high or ultra high levels of fructose. The preferred bait compositions of the instant invention relate to insecticide bait compositions for insect control which contain a ratio of fructose to glucose of no less that about 9:1 and as great as about 10:0.

It is, therefore, the primary object of the present invention to prepare a roach bait composition which is highly effective, yet convenient to use.

It is a further object of the present invention to provide a roach bait which is especially attractive to roaches.

It is still a further object of the present invention to provide a roach bait composition which has no repellency characteristics and which is more attractive to the roaches than otherwise normal known bait formulations.

It is still a further object of the present invention to provide a roach bait which exhibits preferred consumption over prior bait compositions having a general array of sugars and sweeteners as attractants for the roaches.

DETAILED DESCRIPTION OF THE INVENTION AND PREFERRED EMBODIMENTS

Therefore, the present invention provides an improved bait composition for the control of noxious insects, particularly cockroaches, which comprises at least one insecticide selected from the group consisting of organic phosphorus insecticides, carbamates, pyrethroids, boric acid and borates, sulfluramid and avermectins, insect growth regulators and pentadienone hydrazone insecticides; and fructose to glucose ratio in excess of 9:1. The pentadienone hydrazone insecticides can be selected from the pentadiene-3-one substituted amidino hydrazones described by Tomcufik, U.S. Pat. No. 3,878,201, and disclosed by Lovell, U.S. Pat. Nos. 4,087,525 and 4,163,102, the disclosures of which are incorporated hereby by reference thereto, and particularly the compound tetra hydro-5,5-dimethyl-2(1H)-pyrimidinone[3-[4-(trifluoromethyl)phenyl]-1-[2-[4-(trifluoromethyl) phenyl]ethenyl]-2-propenylidene] hydrazone.

The content of the insecticide may vary widely within a range depending upon the individual insecticide used, the species of insect to be treated. Preferably, this invention provides such an insecticide bait composition comprising an insecticide compound, a specific food attractant system, and a binder. A preservative is optionally added to the composition.

Oatmeal is used as a binder in the formulation of insecticidal composition. It is not believed to be a preferred food material for the target insects. Oatmeal has several disadvantages: (1) it contains high levels of microorganisms; (2) is requires dusty grinding for uniformity; and (3) it causes the formulation to harden in about four hours. Thus, a formulation which does not require oatmeal as a binder, but has similar efficacy, would be more advantageous.

Replacing oatmeal with Elmer's glue, a polyvinyl acetate emulsion-based glue, results in acceptable bait efficacy, longer pot life and east of manufacturing. Other substitutes for oatmeal are acetate emulsion-based glue, polyvinyl acetate emulsion, natural glue (beef collagen), gelatin, Carragennan, and water-absorbing polymers. The last two have the advantage of being used as a potential use-up signal since they shrink with loss of moisture. Elmer's glue is an adhesive containing polyvinyl acetate resin emulsion, polyvinyl alcohol, plasticizer, solvent, defoamer, preservative and filler. (Elmer's glue is a commercial product of Borden, Inc.) A stable emulsion product with glue:food attractant ratio of 1:1.6 can be formulated without additional emulsifier. Adding more polyvinyl alcohol emulsifier helps to stabilize a 1:1.80 ratio product. The emulsion is stable for 2–3 days and can be easily redispersed. This emulsion can also be foamed to give a low density bait.

It is preferred that the binder not be repellent to the target insect. Suitable binders include waxes, such as a paraffin, ceresin wax, candilla wax, POLAWAX™, beeswax, carnauba wax, microcrystalline waxes and polyethylene waxes can also be used.

It is to be noted that other materials, such as preservatives, colorings, and the like also may be incorporated into the insecticidal bait composition. It may also be necessary in some instances to render the insecticide more dispersible in the bait composition, and accordingly, materials to accomplish this purpose may also be present in the composition.

The composition of the present invention typically comprises about 0.005% by weight to about 1.0% by weight, preferably about 0.005 % by weight to less than about 0.25% by weight, and most preferably about 0.01 % by weight to less than about 0.25% by weight, of the bait composition. The food attractant(s) will generally comprise the major portion of the composition—typically up to about 80% by weight thereof, with the binder material comprising the remainder thereof—typically from about 5 to 20% by weight. However, in certain instances, depending, inter alia, upon the nature of the various ingredients, the binder material may comprise more of the overall composition than the food attractant(s).

Antimicrobial and/or antioxidant agents also may be included. Optionally, from about 0.5% to about 1.0% of an antimicrobial agent such as sorbic acid/potassium sulfate, Dowcil™ 200 (cis isomer of 2-(3-chloroallyl)3,5,7-triaza-1-azonia-1-adamantane chloride), esters of p-hydroxybenzoic acid such as propyl paraben/methyl paraben (propyl P-hydroxy benzoate/methyl p-hydroxybenzoate), Captan® (N-(trichloromethylthio)-4-cyclohexane-1,3-di-carboximide), sodium silicate, sodium dehydroacetate and sodium benzoate, bromo-nitro propane diods such as 2-bromopropane 1,3-diol, 3-iodo-2-propylbutyl carbamate; and benzothiazolin-2-one may be added as a preservative to inhibit microorganism growth and may be incorporated during formation of the composition of this invention.

Practical and preferred embodiments for preparation of the insecticide compositions containing ultra high levels of fructose and ultra low levels of glucose according to the present invention are illustrated in the following examples.

EXAMPLE 1

One hundred (100) male cockroaches from six German cockroach strains were restrained on their backs. 0.5 droplets of either 1 M fructose or 1 M glucose solutions were applied to the mouthparts of the insects. A positive response was recorded if the droplet was imbibed. Table 1 represents the results of this test. It can be seen from Table 1 that of five strains in this test collected from field locations, 4 showed significantly fewer positive responses to glucose. However, fructose initiated a positive response in 89% or more of the individual insects from all strains. The strain Cyan (cy) is a lab colony, also known as Orlando normal, and not a field strain.

The six German cockroach strains employed in Table 1 were:

TABLE 1

| | % positive response | |
|---|---|---|
| Blattella Strain | fructose 1M | glucose 1M |
| Orlando normal | 89 | 91 |
| Miami | 92 | 88 |
| Torrance | 97 | 33 |
| Hawthorne | 94 | 33 |
| T-164 | 92 | 8 |
| 6133 | 89 | 62 |

EXAMPLE 2

Various ratios of fructose:glucose (1 M total sugar) were prepared in agar. These were introduced along with a blank agar dish into colonies of a field collected strain (T-164) of German cockroach (4 replicates). Test solutions were made by adding crystalline glucose and fructose at the various rates and ratios indicated to total 1 Molar solutions in 1% agar. Two values were 0.5 Molar solutions each for fructose and glucose, respectively. The amount of sugar/agar consumed was measured. Less than 50 percent consumption of the sugar indicated that the sugar inhibited feeding. Fifty percent feeding indicated that the insects were neither inhibited nor stimulated by the sugar. Greater than 50 percent feeding was interpreted as meaning the sugar was a stimulant and enhanced cockroach feeding.

TABLE 2

| Fructose/Glucose Concentration | Percent Cockroaches feeding (Consumption of Fructose/Glucose diet (%)) |
|---|---|
| 1.0M GLU | 5.5 |
| 0.5M GLU | 8 |
| 1:1 | 14.1 |
| 1.5:1 | 14.9 |
| 2.3:1 | 23.6 |
| 4:1 | 37.6 |
| 5.7:1 | 48.2 |
| 9:1 | 53.2 |

TABLE 2-continued

| Fructose/Glucose Concentration | Percent Cockroaches feeding (Consumption of Fructose/Glucose diet (%) |
|---|---|
| 19:1 | 59.4 |
| 0.5M FRU | 70.7 |
| 1.0M FRU | 65.6 |

Table 2 represents the results of Example 2. It can be seen that fructose: glucose ratios of 9:1 and higher stimulate feeding by cockroaches (feeding by more than 50 percent) while those below 9:1 depress or discourage feeding.

EXAMPLE 3

Five corn syrups, which differed in their saccharide composition, were included in two very distinct bait formulations. German Cockroaches were presented with a choice of these baits, and the amount of bait consumed was determined.

The corn syrup compositions were:

TABLE 3

| A | B | C | D | E |
|---|---|---|---|---|
| Fructose 55% | Fructose 0% | Fructose 0% | Fructose 95% | Fructose 100% |
| Glucose 42% | Glucose 5% | Glucose 9% | Glucose 5% | Glucose 0% |
| Higher Saccharides 3% | Higher Saccharides 95% | Higher Saccharides 91% | Higher Saccharides 0% | Higher Saccharides 0% |

The distinct bait formulations were as follows:

TABLE 4

| 1 | 2 |
|---|---|
| Corn Syrup 40% | Corn Syrup 29% |
| Oatmeal | Poultry Liver |
| Carbowax | Soybean Oil |
| Oleic Acid | Oleic Acid |
| Isopropanol | Emulsifier |
| Dowicil | Dowicil |

The percent consumption of each of these distinct bait formulations with each of the five syrups is the following:

TABLE 5

| | % CONSUMPTION OF BAIT TYPE | |
|---|---|---|
| CORN SYRUP | 1 | 2 |
| A | 0.6 | 0.3 |
| B | 3.7 | 13.4 |
| C | 1.1 | 6.4 |
| D | 43.9 | 42.3 |
| E | 50.6 | 37.6 |

The results show that the majority of feeding for both bait formulations is on the materials containing the highest fructose corn syrups. Even though Corn Syrup A contains 55% fructose, the presence of the relatively high percentage of glucose (42%) discouraged consumption of the formulation by the German cockroaches.

FIG. 1 represents efficacy performance of two bait compositions with 100% fructose corn syrup versus corn syrup with fructose and glucose (55:42).

To test ultra high fructose bait formulation efficacy the following test was conducted. Using the bait formulations of Table 4 a representative toxicant was used in a further formulation. That is, an insecticide was added from the class pentadiene-3-one, specifically, tetrahydro-5,5-dimethyl-2(1 H)-pyrimidinone[3-[4-(trifluoromethylOphenyl]-1 -[2-[4-(trifluoromethyl)phenyl] ethynyl]-2-propenylidene] hydrazone The T-164 strain of *B. germanica* was used in this test.

Baits without glucose provided 100% mortality by day 10; however baits with glucose never killed more than 40% of the test insects throughout the 14-day study.

| 100% fructose bait | $LT_{50}$(95% Cl], bait 1 = 3.87 days |
| | bait 2 = 4.08 days |
| fructose/glucose bait | $LT_{50}$[95% Cl], bait 1 = 14.01 days |
| | bait 2 = 16.46 days |

In order to be effective, it has been found that the composition formulation according to the present invention must have an ultra high ratio of fructose to glucose and the amount of fructose (wt. %) of the total formulation must be about 40%. Preferably, the bait composition contains a ratio of about 9:1 to about 10:0 percent by weight of fructose to glucose.

EXAMPLE 4

Two insecticide/corn syrup compositions were tested for efficacy. These two compositions were 0.05% avermectin bait compositions containing the same insecticidal bait, i.e., avermectin, but different attractants. The two attractants were formulated as follows: The "fructose" corn syrup used in this test contained about 95 to about 100 percent by weight fructose, and was sold under the brand name Krystar™. The "fructose/glucose" corn syrup contained 55 percent by weight fructose, 42 percent by weight glucose, and 3 percent by weight higher saccharides, and was sold under the brand name CornSweet™.

The testing arena was two 18"×12"×8" plastic containers attached end-to-end via a ¾" diameter×2" long Tygon tube. A cardboard harborage was placed in one container with 30 German cockroaches (T-164 strain). The test bait was placed in the opposite arena. Free access was provided through the Tygon tube. Water and food was place in both containers. Three replicates per treatment were performed. Dead cockroaches were counted, recorded and removed at each of five time points.

TABLE 6

| INSECTIDE | CORN SYRUP | CUMULATIVE % MORTALITY AT DAY | | | | |
|---|---|---|---|---|---|---|
| | | 1 | 2 | 3 | 4 | 5 |
| avermectin | fructose | 7 | 17 | 33 | 58 | 90 |
| avermectin | fructose/glucose | 1 | 1 | 1 | 1 | 6 |

Table 6 represents the results of Example 4. These results show that the composition comprising avermectin mixed with high fructose corn syrup produced an unexpectedly higher mortality rate when directly compared against a composition comprising avermectin mixed with a fructose/glucose attractant.

The present invention can be implemented in other specific ways than those set forth herein without departing from the spirit and essential characteristics of the invention. The embodiments discussed herein, therefore, are to be considered in all respects as illustrative and not restrictive.

What is claimed is:

1. An insecticidal bait composition comprising about 0.005% by weight to about 1.0% by weight of an avermectin insecticide and a food attractant comprising a saccharide which has a ratio of fructose to glucose in excess of about 9:1.

2. An insecticidal bait composition as claimed in claim 1 wherein said bait composition is a cockroach bait composition and is free of repellancy characteristics.

3. An insecticidal bait composition as claimed in claim 1 wherein said saccharide is free of glucose.

4. An insecticidal bait composition as claimed in claim 1, wherein said insecticide is present in an amount from about 0.005% to about 1.0% by weight of the composition, the food attractant comprises up to about 80% by weight of the composition, and said composition further comprises a binder in an amount from about 5% to about 20% by weight of the composition.

5. A method of controlling insects comprising applying an effective amount of the insecticidal bait composition as claimed in claim 1 to an area containing said insects.

6. A method of controlling insects as claimed in claim 5, wherein said insects are cockroaches.

7. A method of controlling insects as claimed in claim 6, wherein said cockroaches are *Blattella germanica*.

8. A method of controlling insects as claimed in claim 7, wherein said cockroaches are the T-164 strain.

9. An insecticidal bait composition as claimed in claim 1, wherein the avermectin insecticide is present in an amount of about 0.005% by weight to less than about 0.25% by weight.

10. An insecticidal bait composition as claimed in claim 1, wherein the avermectin insecticide is present in an amount of about 0.01% by weight to less than about 0.25% by weight.

* * * * *